United States Patent [19]
Johnson

[11] Patent Number: 6,106,296
[45] Date of Patent: Aug. 22, 2000

[54] METHOD OF ENDODONTIC PREPARATION OF A ROOT CANAL AND A FILE SET FOR USE IN THE METHOD

[75] Inventor: William B. Johnson, Tulsa, Okla.

[73] Assignee: Tulsa Dental Products Inc., Tulsa, Okla.

[21] Appl. No.: 08/896,381

[22] Filed: Jul. 18, 1997

Related U.S. Application Data

[63] Continuation of application No. 08/788,479, Jan. 28, 1997, abandoned, which is a continuation of application No. 08/373,626, Jan. 17, 1995, abandoned.

[51] Int. Cl.[7] ................................................. A01C 05/02
[52] U.S. Cl. ........................ 433/224; 433/102; 433/224
[58] Field of Search .................................... 433/102, 224

[56] References Cited

U.S. PATENT DOCUMENTS

| | | | |
|---|---|---|---|
| 5,257,934 | 11/1993 | Cossellu | 433/102 |
| 5,658,145 | 8/1997 | Maillefer et al. | 433/102 |
| 5,746,597 | 5/1998 | Maillefer et al. | 433/102 |
| 5,836,764 | 11/1998 | Buchanan | 433/102 |

*Primary Examiner*—Nicholas D. Lucchesi
*Attorney, Agent, or Firm*—James B. Bieber

[57] ABSTRACT

A method of cleaning and shaping a root canal in a tooth in preparation for filling the root canal with a filler material, such as gutta percha, as a part of an endodontic procedure includes the step of inserting into the root canal a tapered file having a spiraled scraping edge formed thereon, the scraping edge having a neutral rake angle, the file having a taper of about 0.04% such that, as a sequence of files of the same characteristics but having different tip diameters are employed, the root canal is shaped and cleaned from the coronal area towards the tooth apex in contrast to the traditional endodontic procedure wherein root canals have been shaped and cleaned in the step back method beginning with the root canal apex and progressing towards the coronal area.

16 Claims, 5 Drawing Sheets

STEP 1

Fig. 1  Fig. 2  Fig. 3  Fig. 4

Fig. 5  Fig. 6  Fig. 7 STEP 1

Fig. 8
STEP 2

Fig. 9
STEP 3

Fig. 10
STEP 4

*Fig. 13* STEP 7

*Fig. 12* STEP 6

*Fig. 11* STEP 5

METHOD OF ENDODONTIC PREPARATION OF A ROOT CANAL AND A FILE SET FOR USE IN THE METHOD

This application is a continuation of application Ser. No. 08/788,479, filed Jan. 28, 1997, now abandoned, which is a continuation of application Ser. No. 08/373,626, filed Jan. 17, 1995, now abandoned.

PRIOR ART

Cleaning and shaping root canals with files, and particularly with tapered files having at least one spiral groove thereon, is well known. For reference to background material relating to the use of metal tapered files having spiral grooves formed thereon reference may be had to U.S. Pat. No. 4,934,934 that issued Jun. 19, 1990 entitled "Dental File/Reamer Instrument" and U.S. Pat. No. 5,106,298 that issued Apr. 21, 1992 and entitled "Endodontic Dental Instrument". Both of these patents, and the references cited in them, are incorporated herein by reference.

U.S. Pat. No. 5,106,298 is particularly relevant to the method of this invention. This patent discloses a tapered file having a proximal portion and an apex end and having at least one spiral groove formed thereon extending from the proximal portion to the apex end. The file described in this patent is important in that it teaches a groove or grooves forming scraping shoulders that intersect the peripheral surface of the drill at an angle of about 90° to a tangent to the drill surface at the point of intersection. This angular relationship between the shoulder of the groove and the peripheral surface of the drill is commonly referred to as a neutral rake angle. This neutral rake angle is important in the practice of the method of the present invention in that a tapered drill with one or more spiral grooves forming scraping shoulders having neutral rake angles function to clean and shape a root canal as the file is rotated in the root canal without tending to grab or engage the root canal in a screw like action. That is, rotation of a tapered drill having grooves forming a neutral rake angle tends to remove the pulp and clean the interior of the tooth and shape it without the file tending to self-thread itself aggressively towards the apex of the root canal.

BRIEF SUMMARY OF THE INVENTION

This invention relates to an improved method of preparing a root canal in a tooth to receive endodontic filler material. A root canal and tooth has a proximal portion and an apex portion. The method includes the steps of manipulating tapered files in the root canal, the files being a part of a set in which each file has a taper greater than 0.02 millimeters increase in diameter for each millimeter of length and in which the files of the set have tip diameters that are separated from each other by a selected size progression, and in which the files have scraping surfaces each having a neutral rake angle. By the method of this invention, files are selected for manipulation in a root canal so that the root canal is cleaned and shaped essentially from the coronal area of the tooth in the direction towards the tooth apex. The method of this invention is contrasted with the typical and long practiced endodontic procedure wherein root canals have historically been treated by the use of files constructed and dimensioned to clean a root canal starting essentially with root apex followed by the use of increasingly larger sizes of files so that the cleaning and shaping action takes place from the apex towards the coronal area.

More specifically, the invention is related to a method of cleaning and shaping a root canal in a tooth in preparation for filling the root canal with a filler material, such as gutta percha, as a part of an endodontic procedure. A root canal of a tooth has a proximal portion adjacent the tooth crown or enamel bearing coronal area. The root canal progresses towards the root apex from which the nerves extending from channels in the jawbone enter into the tooth.

More particularly, the method of this invention is practiced by the practitioner first drilling a hole in the tooth crown and into the pulp chamber to provide access to the root canal proximal portion. A first file is inserted into the root canal proximal portion, the first file being selected from a set of files so that the diameter of the file is such that initial contact is made between the spirally formed scraping edge and the proximal portion of the root canal to first clean and shape the proximal portion.

Thereafter, a second file is selected of a tip diameter that, when inserted into the root canal, contacts the portion of the root canal adjacent to the first mentioned proximal portion. The selection of files having different apex diameters from the set and manipulation thereof in the tooth is continued until a file apex end reaches the apex of the tooth.

The cleaning and shaping of the root canal thus proceeding from the coronal area of the tooth in the direction towards the tooth apex.

A set of files as used in practicing the method of this procedure preferably has tip diameters that progress in a series from the smallest to the largest, each step representing an increase in tip diameter of a selected arithmetic or geometric size progression. The typical file set may have nine files, the tip diameters ranging from approximately 0.129 mm to 1.0 mm. In the typical endodontic procedure of this invention only four or five files of this set are employed. The size ranges of the files used for an endodontic procedure is determined by the root canal characteristics. A size progression of, by example, 29% has functioned well in experimental applications.

While the procedure of cleaning and shaping a root canal as a part of an endodontic process of this invention can be carried out by manually manipulating files when positioned in a root canal, the preferred procedure is to support the proximal end portion of each file in a power driven hand piece that is manipulated by the practitioner (endodontist or dentists) in which the practitioner, after placing a file in a hand piece, positions the file in a root canal and energizes the hand piece to rotate the file. The practitioner applies only gentle pressure on the file as it is rotated in a root canal, it being a characteristic of the files of the set that as a file shapes and cleans a portion of a root canal it will advance in the canal until the file has formed a substantially circular root canal shape at the file apex. Where further advancements does not easily take place or when easy advancement of the rotating file ceases, the practitioner knows that a different size file needs to be selected to shape and clean a different portion of the length of the root canal. The rotating file brings the tooth pulp tissue and dentinal debrish coronally where they can be easily removed.

DESCRIPTION OF THE DRAWINGS

FIG. 5 and 6 show the external appearance to files as employed in the invention, the files having head portions that are constructed and dimensioned to be received in a hand piece (not shown) as typically used by dentists and endodontists. FIGS. 5 and 6 show two different size files.

FIGS. 7 through 14 show the sequence of steps employed in practicing the method of this invention. Specifically, FIGS. 7 through 14 each show a file positioned in the root canal of a typical tooth and illustrate the sequence of steps whereby a typical root canal in a tooth is cleaned and shaped in the direction from the root coronal area to the root apex.

DETAILED DESCRIPTION OF THE PREFERRED EMBODIMENT

Figure 17:
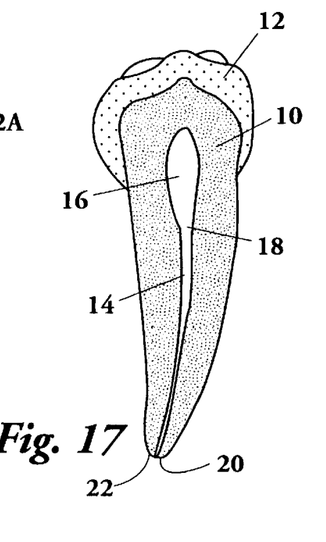
FIG. 17 shows the tooth as illustrated in FIGS. 7 through 16 as the tooth typically appears in cross-section prior to the initiation of an endodontic procedure.

Referring first to FIG. 17 a typical tooth is illustrated in cross-section as an example of a tooth as it appears prior to the initiation of an endodontic procedure. Endodontic procedures are typically carried out when a tooth becomes abscessed, that is, when the pulp material formed in the tooth root canal becomes infected. The tooth as illustrated in FIG. 17 includes a dentin portion 10 that forms the body of the tooth. Formed on the upper exterior of the tooth is the enamel 12 that is the hard outer portion of the crown area of the tooth which is visually exposed. Inside dentin 10 there is a root canal 14 that is enlarged in the upper portion within the crown, the enlarged portion being termed the pulp chamber 16. The transition from the pulp chamber 16 to the root canal proper is termed the orifice area 18. The root canal ends at the tooth apex 20 at a root canal apex opening 22 through which the apical foramen (not shown) passes to connect the pulp material that constitutes the tooth nerve with the plexus of nerves in the jaw bone structure (not shown). The root canal 14, including the pulp chamber 16, in a healthy tooth is filled with pulp material that is essential during the tooth growth. When a tooth has reached maximum size the function of this pulp material diminishes and it can become infected—typically termed an abscess—which can be exceedingly painful. In the past, when the pulp material in a tooth root canal or pulp chamber become infected there was no recourse other than to extract the tooth. In present day dentistry tooth extraction is required much less frequently. Due to the advancement of the science of endodontics an abscessed tooth can usually be preserved to the great benefit of the patient. To preserve the tooth, the pulp material in the pulp cavity 16 and root canal 14 must be carefully removed and the root canal cleaned. The canal cannot be left open but must be filled with a filler material to prevent body fluids from entering the root canal after the pulp material has been removed. The technique of removing the pulp material from root canal 14, including pulp center 16, and replacing it with a hygienic filler material, such as gutta percha, to enable the tooth to remain in the body and free of pain to the patient, is the basic practice of endodontics. This invention is concerned with an improved method of cleaning and shaping the root canal 14.

Herebefore, a common practice of endodontics is to clean the root canal in a process generally termed the "step back" method. In this method the practitioner first selects a file from a set in which the files have a 0.02 taper, the first file being selected to have a tip diameter so that tip will substantially reach to the root canal apex opening 22 to first clean the apex area. Subsequently, the practitioner selects files of increased cross-section, that is, files of essentially the same 0.02 taper but of greater diameter, to progress upwardly towards the coronal area to enlarge and shape the root canal, each file cleaning the root canal primarily by engagement with the root canal by the portion of the file adjacent the file tip. Since the technique is carried out essentially from the bottom of the tooth, that is, from the apex area of the tooth towards the coronal area, the method is called "step back". In contrast, the method of this invention is the opposite, that is, the procedure that will be described herein is a "crown down" approach.

For the purpose of carrying out the method of this invention a set of dental files is required that is different than the set of dental files utilized in the "step back" method. FIGS. 1 through 4 illustrate four files taken from a set employed in the present invention. The four files of FIGS. 1 through 4 are taken from a set of files which typically includes nine sizes, usually identified as sizes number 2 through number 10.

Each of the files 24A through 24D of FIGS. 1 through 4 consist of a main body portion having spiral grooves 26 formed thereon, the grooves forming spiral lands 28. The body portion of each of the files extends from an apex 30 to a file proximal portion 32. The proximal portion has an enlarged diameter portion that forms a shank 34, only a portion of which is seen in FIGS. 1 through 4. Shank 34 is shaped and dimensioned to be received in a typical hand piece that is commonly employed by dentists and endodontists. A typical hand piece (not shown) has provision for selectively imparting rotation to a file retained in it. The dentist or endodontist employs the hand piece for inserting a file into a root canal and for rotating the file in a method that will be described in detail subsequently.

Figure 1:
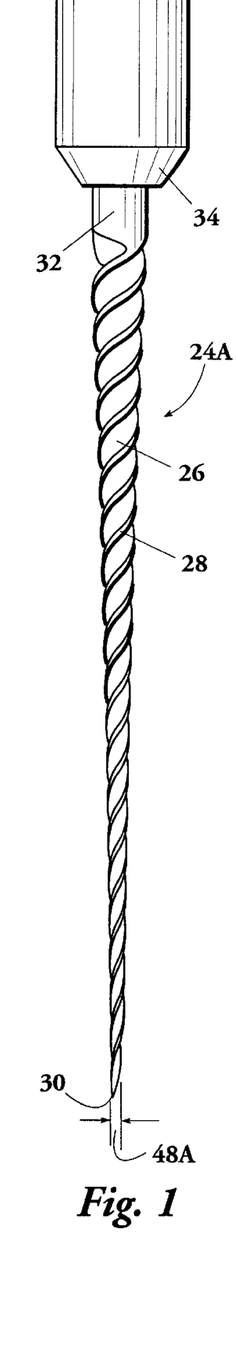
FIGS. 1 through 4 show representatives of portions of dental files that are used in practicing the method of this invention. The four files illustrated in FIGS. 1 through 4 are a part of a set of dental files for use in practicing the method, the typical set consisting of approximately nine files that are preferably substantially identical to each other in degree of taper and cleaning shoulder structure but differing from each other in that the diameter of the tips are progressively larger in a geometrical progression.
Figure 2:
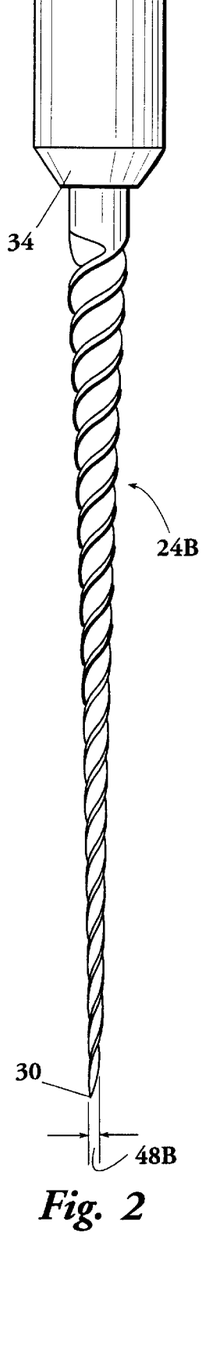
Figure 3:
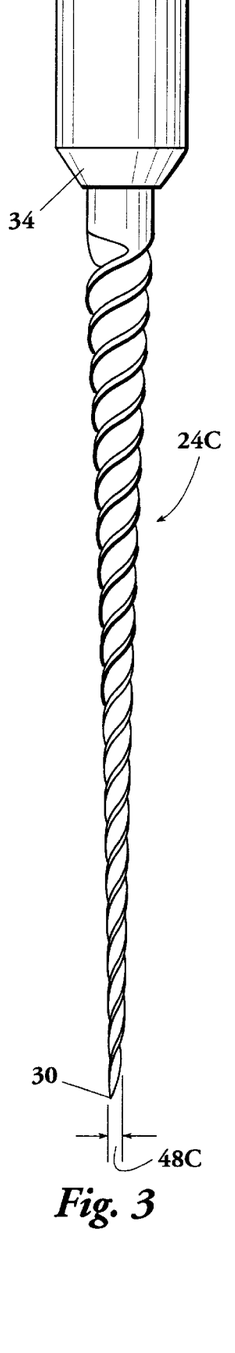
Figure 4:
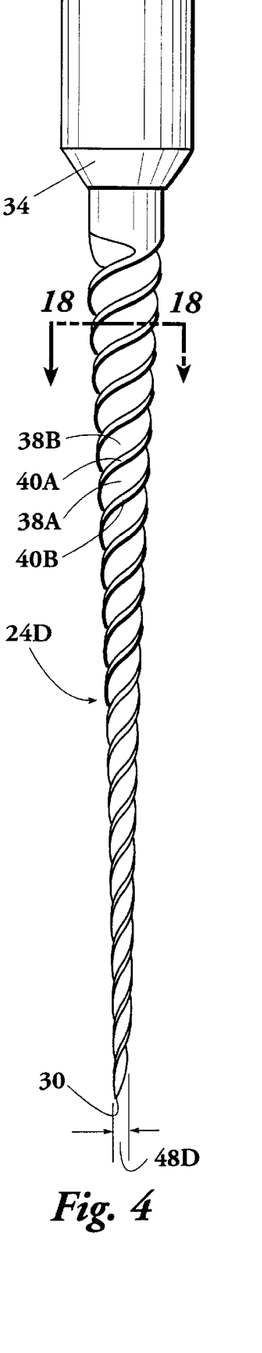
Figure 18:
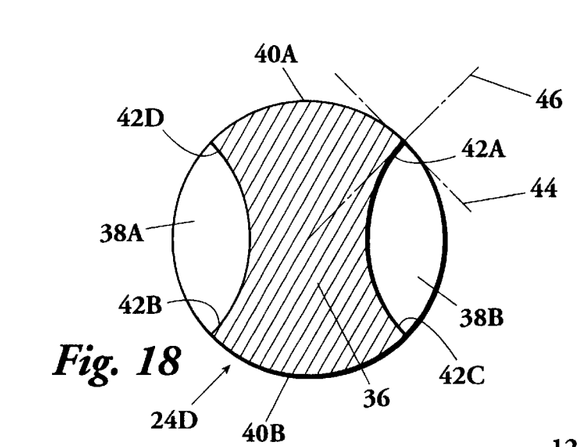
FIG. 18 is a highly enlarged cross-sectional view of a file as typically employed in practicing the method of this invention, taken along the line 18—18 of FIG. 4. This figure shows how the flutes are formed in a way to provide scraping shoulders having neutral rake angles. The number of spiraled flutes can vary from two to four or five or more, with radial lands existing between the flutes.

FIG. 18 is a cross-sectional view taken of file of FIG. 4 that represents the cross-sectional arrangement of all of the files making up a set of files used to practice the method of this invention. The file 24D as shown in FIG. 18 has a body portion 36 that is formed of strong yet flexible metal. Into this tapered body is machined at least one spiral groove. In the embodiment illustrated in FIG. 4 and FIG. 18, the file is formed with two intertwining spiral grooves 38A and 38B. Between the grooves 38A and 38B are the circumferential lands 40A and 40B that form the exterior of the file before grooves 38A and 38B are machined. Where groove 38B intersects land 40A a scraping shoulder 42A is formed. In like manner, where groove 38A intersects land 40B a scraping shoulder 42B is formed. Each of these scraping shoulders 42A and 42B is formed so that a tangent of the arc of groove 48B intersects a tangent of circumferential land 40A at right angles as indicated by the dotted lines 44 and 46. This forms what is called a "neutral rake angle". By "neutral rake angle" is meant that the scraping surface 42A scrapes a portion of a root canal that it contacts without a tendency to cut into the root canal surface as would be caused by a positive rake angle, such as is employed in drill bits. A negative rake angle which would tend to slide over the surface of a root canal without scraping or shaping it. Thus, the employment of a neutral rake angle in the file set used in the method of this invention is critical, however, obviously the actual angle can depart very slightly from exactly 90° as represented by the dotted lines 44 and 46, but for optimum results the rake angle as indicated by the dotted lines 44 and 46 should be approximately a right angle.

Figure 8:
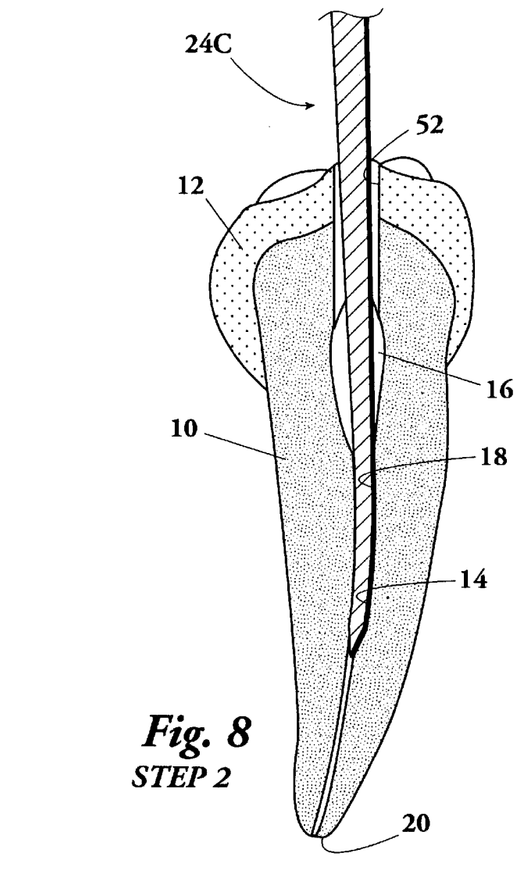

Shoulders 42C and 42D are formed as shown in FIG. 18, however, if the file is rotated only in one direction while in a root canal, such as clockwise in the cross-sectional view of FIG. 8, the shoulders 42C and 42D do not perform any function, that is, they do not scrape nor do they take any part in the shaping of the root canal. In the typical application of this invention it is not necessary to reverse the rotation of a file while in a root canal, however, if a file should inadvertently become stuck in a root canal it can augment the extraction of the file in some instances by rotating it in the opposite direction. Thus, the surfaces 42C and 42D would function primarily, if used at all, to assist in extracting the file from a root canal but do not play any part in the cleaning and shaping of a root canal.

The files making up a set are essentially identical to each other, as previously indicated, except for a change in the apex diameter. The apex diameter of the file of FIG. 1 as indicated by the numeral 48A; the apex diameter for the file of FIG. 2 by 48B; the apex diameter of file of FIG. 3 by 48C; and the apex diameter of the file of FIG. 4 by 48D. The apex diameters vary from each other by a fixed arithmetic or geometrical progression. In a preferred embodiment of this invention the set of files have apex diameters that vary geometrically by a ratio of about 29%. That is, the apex diameter 48B is 29% greater than the apex diameter 48A of file 24A. In like manner, the apex diameter 48C of file 24C is approximately 29% greater than the apex diameter of 48B of file 24B, and so forth. Obviously, some other percentage of size change could be selected or the tip diameters 48A through 48D can vary by a fixed amount, such as 0.05 millimeters. In order for a dentist or endodontist to easily identify file sizes the shank portions 34 are typically color coated. The typical apex diameters of files making up a set of files as employed in the preferred practice of the method of this invention are as follows:

| SIZE | DIAMETER IN MILLIMETERS | COLOR CODE |
| --- | --- | --- |
| 2 | .129 | White |
| 3 | .167 | Yellow |
| 4 | .216 | Red |
| 5 | .279 | Blue |
| 6 | .360 | Green |
| 7 | .465 | Brown |
| 8 | .600 | White |
| 9 | .775 | Yellow |
| 10 | 1.000 | Red |

Figure 5:
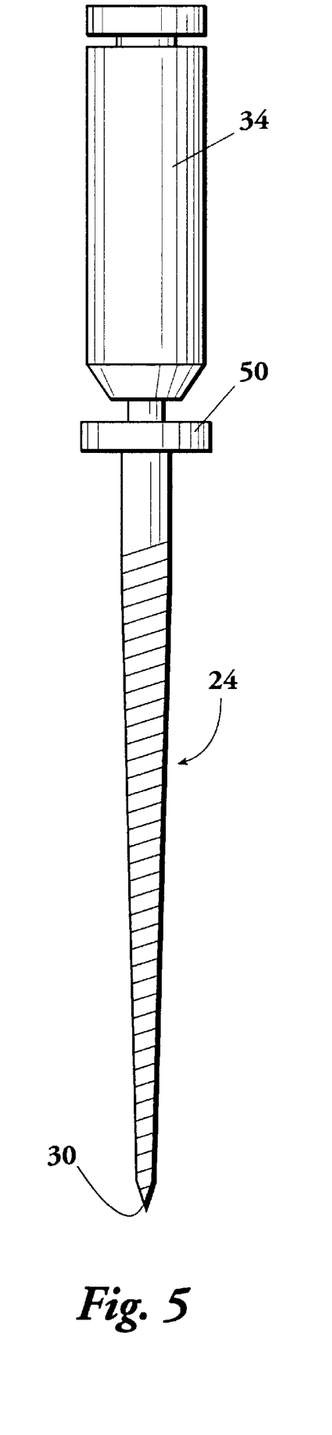
FIGS. 5 and 6 show files as used in practicing the method of this invention wherein the file contour is shown diagrammatically.
Figure 6:
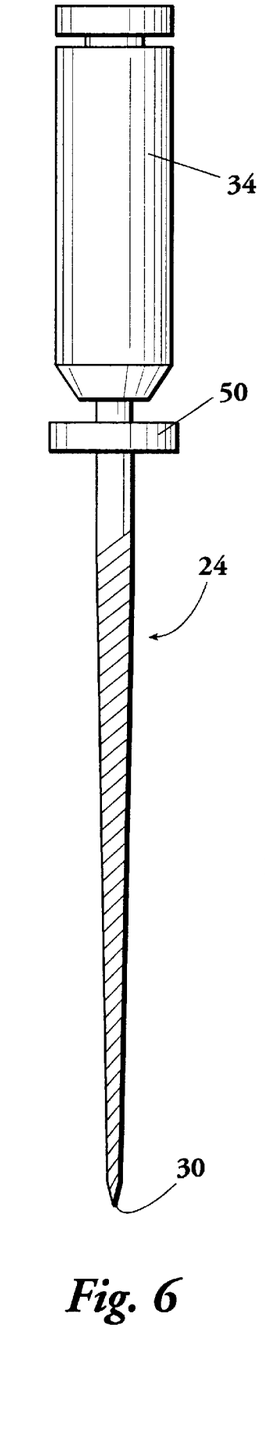

FIGS. 5 and 6 show elevational views of endodontic files as used in practicing the methods of this invention, the body portions of the files being shown diagrammatically and the shank portions 34 being illustrated in greater detail. The shanks are typical of those employed on other dental files and dental drills, the shanks being receivable in hand pieces as commonly used by dentists and endodontists. The files shown in FIGS. 5 and 6 include an elastomeric washer 50 that are slidably positionable on the files. These washers 50 are utilized to gauge the spacing between the washers and the file apexes 30 so the dentist or endodontist can know the depth of the file in a root canal.

Figure 7:
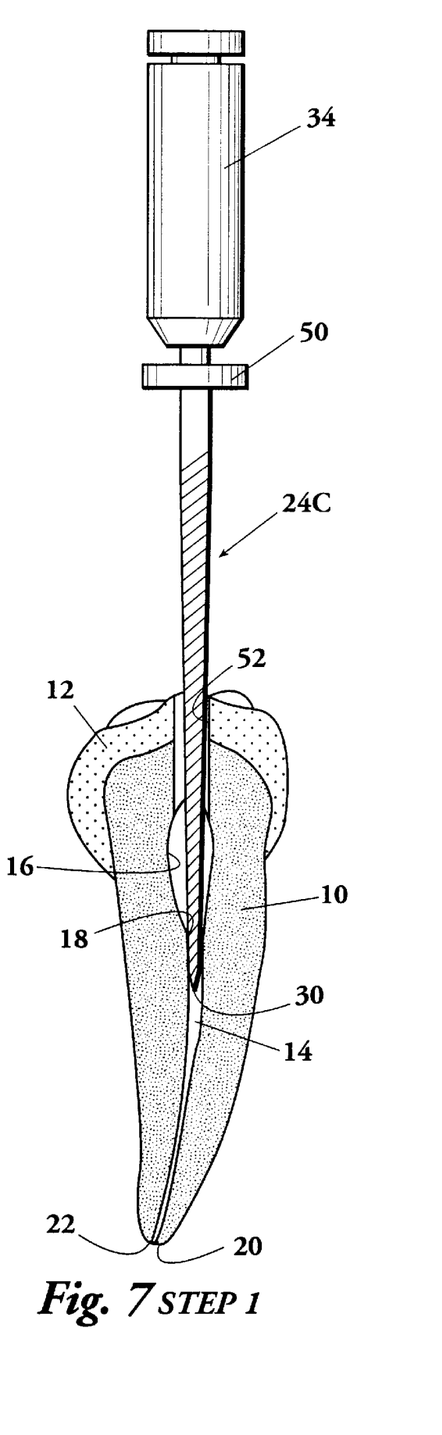

FIGS. 7 through 14 illustrate the sequence of steps employed to endodontically prepare a typical tooth, such as an incisor or canine. The first step is illustrated in FIG. 7. In this first step the practitioner (endodontist or dentist) drills a hole 52 through the crown enamel 12 into the pulp chamber 16 to expose the root canal 14. The root canal and pulp chamber then must be cleaned and shaped so that the interior of the tooth can be filled with a filler material such as gutta percha. After hole 52 is drilled a file 24 is inserted into the root canal. The file 24 is selected to be of a size that the portion thereof four or five millimeters up the file shaft from the tip 30 engages the sidewall of the orifice area 18 of the root canal. That is, in the method of this invention, contrary to an endodontic procedure in common present use, the practitioner selects a relatively larger file size such as a number 4 or whatever intermediate sizes is required to engage the upper portion of the root canal 14. In contrast, a common procedure that has long been practiced calls for the practitioner to select a small diameter file that penetrates substantially to the tooth apex 20 to first clean the area of the root canal adjacent the apex opening 22. Following the currently used procedure the practitioner would then gradually increase file diameter size to enlarge and shape the root canal starting from the tooth apex 20 and working upwardly in what is known as "step back" procedure. The present procedure is the opposite, that is, file 24C is of a relatively larger size, that is one that is normally much larger than would be feasible to extend all the way to or adjacent the apex opening 22 as the first step in the procedure. The larger file shown in FIG. 7 is employed to clean and shape the upper portion of the root canal 14, that is, the portion at the orifice area 18 that communicates the root canal with the pulp chamber 16.

In step 2 as shown in FIG. 8, file 24C has been advanced in the root canal typically using the same size file as in step 1, such as a No. 4. Using the type of file as previously discussed with reference to FIG. 18, the practitioner will find that when the file has advanced to the point where the canal has been cleaned and shaped in proportion to the size of the file selected so that the portion of the file engaging the root canal shapes the root canal to substantially circular cross-sections, and the circular cross-sections extend to the file apex 30, the file will not easily further advance. The practitioner can tactically determine after a short amount of practice when a file has performed its function and a different size file is required to further downwardly advance the cleaning and shaping action in the root canal.

Figure 9:
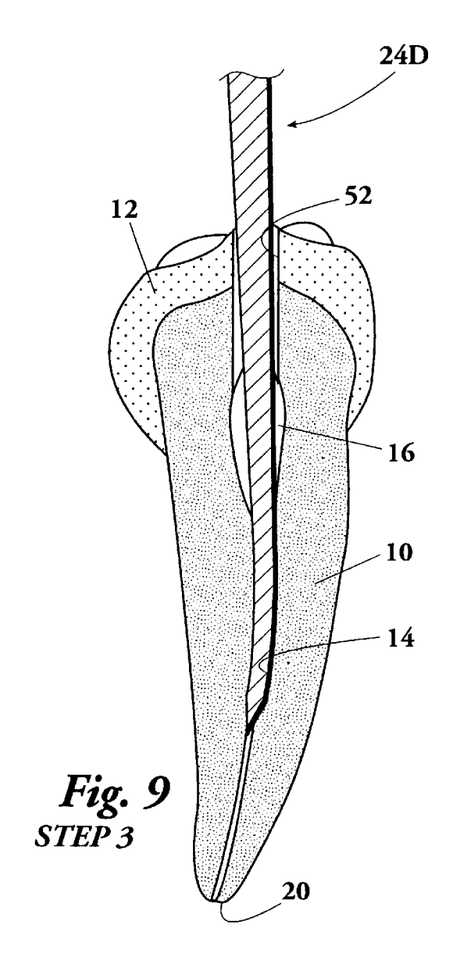
Figure 10:
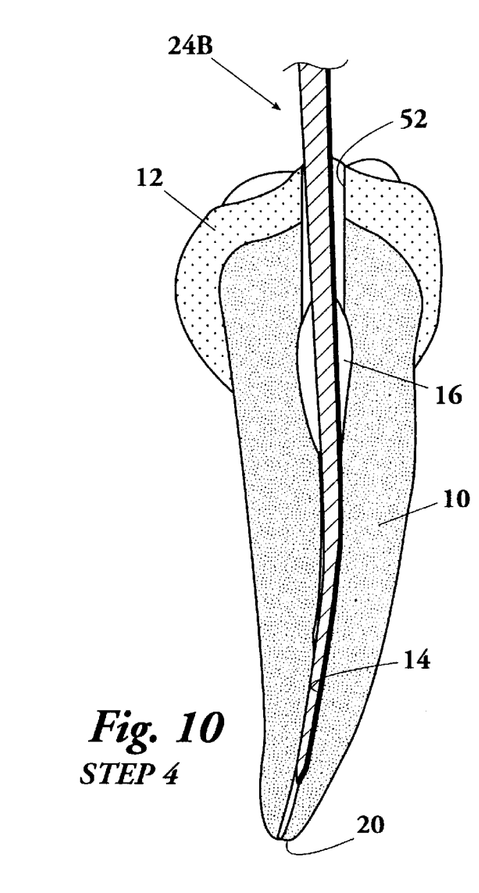

Step 3, FIG. 9, shows the use of a larger size file such as a No. 5, indicated by 24D. The larger size file further cleans and shapes the upper portion of the root canal. In step 4, FIG. 10, the practitioner employs a smaller size file, such as a size 3, to extend the shaping and cleaning action farther into the root canal. In step 5, FIG. 11, a number 2 size file 24A has been selected by the practitioner, the size being such as to extend the cleaning and shaping action all the way to apex 20. Thus, it can be seen that in steps 1 through 5 the technique has employed larger size files followed (but not necessarily in strict sequence size order) by smaller size files to shape the root from the top down, that is, from the orifice area adjacent the pulp chamber 16 to root apex 20 as contrasted with a currently used procedures of shaping the root canal from the apex upward.

Figure 11:
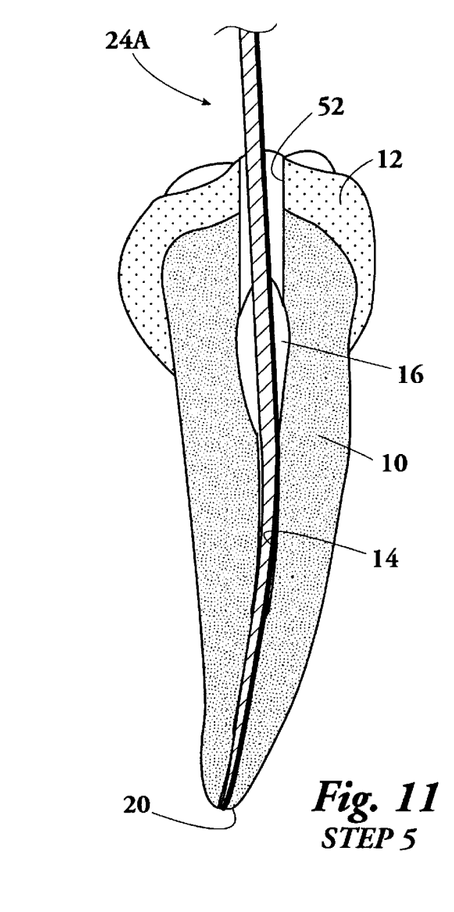
Figure 12:
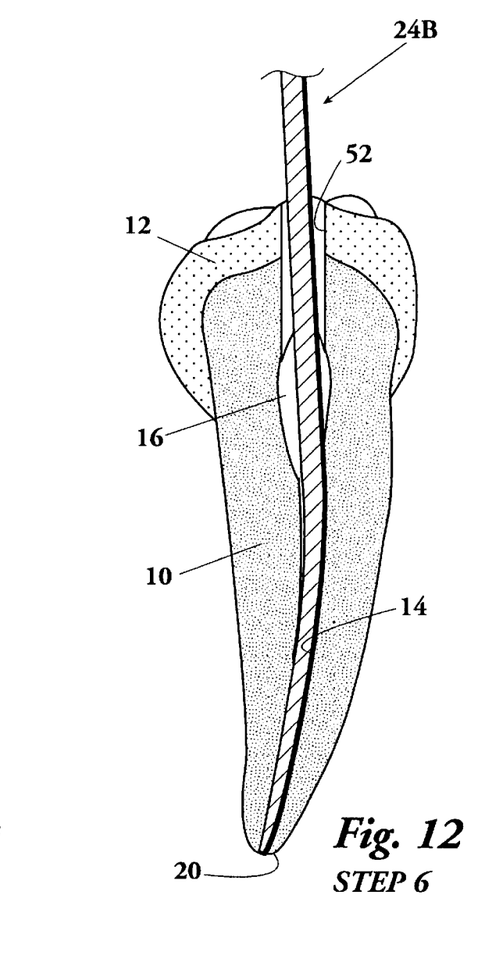
Figure 13:
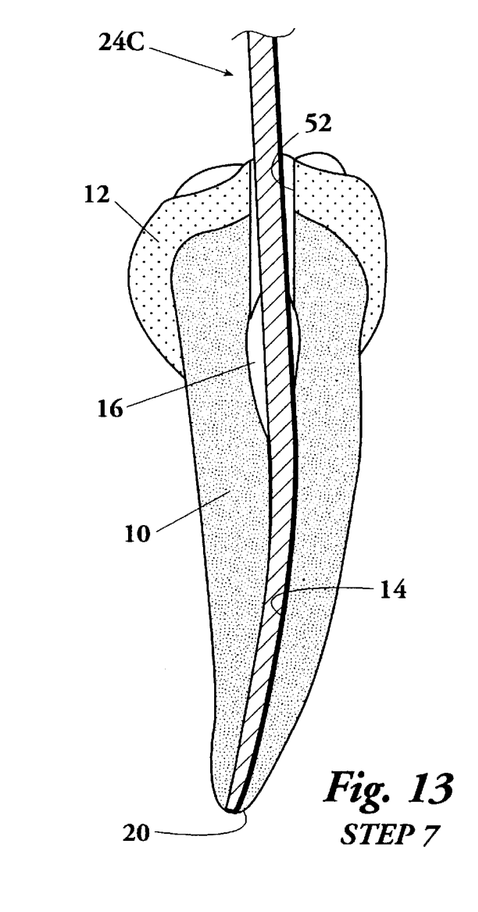
Figure 14:
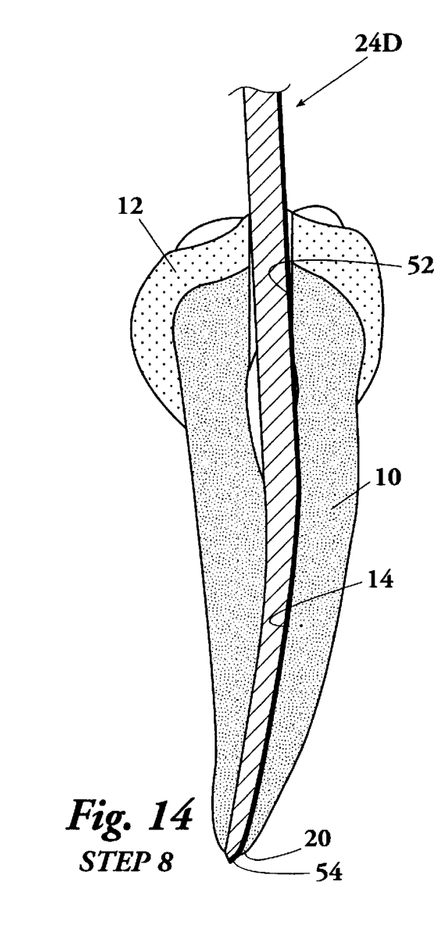

After size 2 file, as an example, has been used in step 5, FIG. 11, a size 3 file 24B is then employed to further shape and clean the canal. In step 7, FIG. 13, the practitioner has employed a size 4 file 24C that is, the same size file as was used in the initial step 1, to further enlarge and shape the root canal from the coronal area all the way to the tooth apex 20. Finally, in step 8, FIG. 14, a size 5 file 24D is employed to shape the root canal all the way to the root apex to the size appropriate for filling with a filler material.

Figure 15:
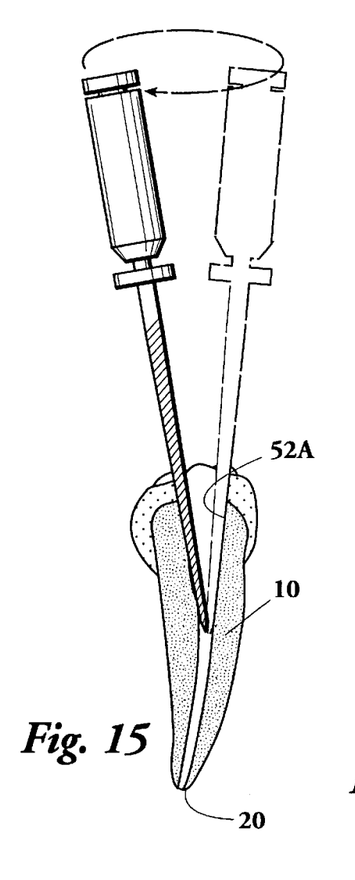
FIG. 15 shows a final step of flaring the upper portion in the area of the pulp chamber and the opening through the tooth crown to facilitate placement of a filler material, such as gutta percha, in the fully cleaned and shaped root canal.

After the root canal has been cleaned and shaped in steps 1 through 8 as illustrated in FIGS. 7 through 14, the practitioner then typically flares the opening through the crown as shown in FIG. 15. The size of the file used in the flaring action is not critical and in fact, a different kind of file may be employed for the flaring action of FIG. 15 if desired, that is, to flare the original opening in the tooth until it has the shape of opening 52A may best be accomplished utilizing a standard K type file that is of the type that has typically been employed in the endodontic profession. Such files have greater auguring action than the type of files as illustrated in FIG. 18 and the type of files which, according to the principles of this invention, are preferably used for practicing steps 1 through 8.

Figure 16:
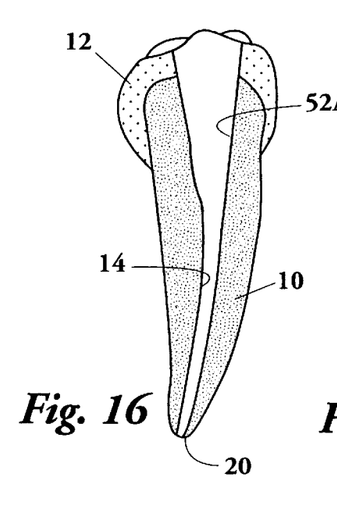
FIG. 16 shows the tooth with the root canal cleaned and shaped, and the coronal area flared, the tooth being ready to receive filler material.

FIG. 16 shows the completed tooth that has been shaped and formed and is ready to receive filler material. The filler material can be applied in a variety of ways, however, a preferred method of filling the cleaned and shaped root canal is by the use of endodontic obturators of the type illustrated and described in U.S. Pat. No. 4,758,156; 4,894,011; 5,118,297 and 5,149,268. However, it is understood that the method of filling the root canal is not a part of this invention which is concerned only with the method of cleaning and shaping the canal and the set of dental files used in practicing the method.

While the basic concepts of the invention is illustrated in Steps 1 through 8 (FIGS. 7 through 14) can theoretically be practiced irrespective of the specific characteristics of the endodontic files being used, it has been determined that successful practice of the method described herein is best achieved by using files having two characteristics that are different than files that are commonly used in the dental profession. First, the files preferably are the type as illustrated in FIG. 8 wherein the scraping shoulders of the file have a neutral rake angle—that is, wherein the files used do not have a screw type action when rotated in a root canal that tend to forcibly advance the file downwardly in the root canal. The second highly desirable characteristic of the files that is different than those commonly used in the dental profession is that the files have a greater angle of taper. The typical files long used in the dental and endodontic profession have employed a 0.02 taper, that is, for each one millimeter of axial length, the diameter of the file increases by 0.02 millimeters. In practicing the methods of this invention it has been determined that files having a taper that is greater than 0.02 that provides superior and much more effective results. Thus, there is an interrelationship between the technique of cleaning and shaping root canals in the coronal down method and the use of files having neutral rake angles and greater than 0.02 tapers. Files have a rate of taper of 0.04 millimeters per millimeter of length, that is, a 0.04 taper, have performed extremely well in practice.

A unique aspect of the method of this disclosure is the discovery that a file being a taper greater than 0.02 and having neutral rake angle shaping surfaces will, when operated in a root canal, plane the root canal so that, where contacted by the file, the root canal develops circular or substantially circular cross-sectional shapes. Further, that the file can be axially easily advanced in the direction towards the tooth apex until the file tip end forms the root canal into a circular or substantially circular cross-sectional shape, after which the file cannot be axially advanced further towards the tooth apex without the application of additional axial force. The fact that additional axial force is required to cause further advancement is easily noticeable by the practitioner and serves as a tactile signal that it is time to replace the file with one of a different size. The process is repeated until a file tip easily advances to the tooth apex. The rotating files bring the tooth pulp tissue and dental debrish coronally where they can be easily removed.

A unique aspect of a file of the type described herein that has radial lands (40A and 40B, FIG. 4) forming edges (42A and 42B, FIG. 18) with neutral rake angles, and that has a tip end 30 formed by a standard conical shape 54 (see FIG. 14) is that the file does not tend to laterally transport. That is, file tip end 30 does not tend to dig into the sidewall of a root canal since the provision of radial lands and edges having neutral rake angles does not form the sharp cutting edges associated with files having bi-directional cutting edges that produce sharp cutting points when a typical conical end shape is formed at the file apex. In order to overcome the tendency of bi-directional cutting files to laterally transport when the file is rotated in a root canal, others have suggested a special rounding treatment to the file tip, to round off the intersection between the bi-directional cutting edges and a conically shaped end point. Such special treatment or rounding off is not required with a file having radial lands between grooves providing neutral rake angles as described herein.

The invention has been described here in utilizing four different size files, that is, sizes 2(24A) through size 5(24D). As previously indicated, the standard file set includes nine sizes, that is sizes 2 through 10. The particular range of sizes employed for cleaning and shaping a root canal using the methods disclosed herein will depend upon the characteristics of the root canal. Obviously, root canals that are inherently larger will employ a larger group of sizes. Further, while the invention has been described utilizing only four sizes of files available out of a set of nine, some procedures may require as few as three sizes or as many as six or seven sizes to complete cleaning and shaping of the root canal depending upon the characteristics of the canal.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

Whereas, the present invention has been described in relation to the drawings attached hereto, it should be understood that other and further modifications, apart from those shown or suggested herein, may be made within the spirit and scope of this invention.

What is claimed is:

1. An improved method of cleaning and shaping a root canal in a tooth in preparation for filling the root canal with a filler material, such as gutta percha, as a part of an endodontic procedure, the root canal having a proximal portion adjacent the tooth pulp chamber and tapering to an apex portion adjacent the tooth apex, the root canal having a characteristic rate of taper, comprising the steps of:

inserting into the root canal a first file having spiraled scraping edges formed thereon, the file having a proximal end and a distal end, the file being tapered from adjacent said proximal end to said distal end, the rate of taper being greater than said characteristic rate of taper of said root canal;

rotating and axially advancing said file within said root canal to clean and shape said root canal, the relative rate of taper of said file relative to said root canal characteristic taper being such that said root canal is shaped, at least in significant part, by first cleaning and shaping the root canal proximal portion; and using additional files of different diameters, each said file having the same rate of taper as said first file and otherwise similar to said first file, for advancing the cleaning and shaping action from the root canal proximal portion to the root canal apex portion.

2. The method according to claim 1 wherein said file has a taper greater than 0.02 millimeters in diameter per millimeter of axial length.

3. The method of claim 1, wherein said files are formed of a strong, flexible metal.

4. A method of cleaning and shaping a root canal in a tooth having a crown, pulp chamber and apex, in preparation for filling the root canal with a filler material, such as gutta percha, as a part of an endodontic procedure, the root canal having a proximal portion adjacent the tooth pulp chamber and tapering to an apex portion adjacent the tooth apex, the root canal having a characteristic rate of taper, comprising the steps of:

drilling a hole in said tooth crown and into said pulp chamber to provide access to said proximal portion of said root canal;

inserting into said root canal a selected file taken from a set of files, each file having a proximal portion and a distal end, each file tapering from said proximal portion to said distal end, each file having at least one cutting edge formed thereon, all files in said set having an identical taper exceeding said root canal characteristic taper and different distal end diameters; and rotating said selected file in said root canal to scrape away and remove pulpal material and to shape and clean said root canal in preparation for receiving filler material, the rotation of the file being continued as the file is axially advanced towards the tooth apex until the file resists further axial advancement following which a different file having a different diameter is selected from said set of files, the procedure being repeated until the root canal is cleaned and shaped, the procedure taking place primarily in the direction from said proximal portion towards said apex portion.

5. The method according to claim 4 wherein said files each have a taper greater than 0.02 millimeters per millimeter of axial length.

6. The method of claim 5, wherein said files each have a taper of about 0.04 mm per mm of axial length.

7. A method of preparing a root canal in a tooth to receive endodontic filler material, the root canal having a proximal portion and an apex portion, comprising the steps of rotating and advancing tapered files in the root canal, the files having a uniform degree of taper selected so that the files clean and shape the root canal progressively from said canal proximal portion towards said apex portion, wherein said file taper is 0.04 mm per mm of axial length.

8. A method of cleaning and shaping a root canal in a tooth in preparation for filling the root canal with a filler material, such as gutta percha, as a part of an endodontic procedure, the root canal having a proximal portion adjacent the tooth pulp chamber and tapering to an apex portion adjacent the tooth apex, the root canal having a characteristic rate of taper, comprising the steps of:

(a) drilling a hole in said tooth and into said pulp chamber to provide access to said root canal proximal portion;

(b) inserting into said root canal proximal portion a first file selected from a set of files, each file in said set having a proximal portion and a distal end portion, each file in said set having spiral grooves providing shoulders with substantially neutral rake angles, each file in said set tapering from said distal end towards said proximal portion at a selected rate of taper, each file in said set having a selected tip diameter, the tip diameter of the files in said set increasing at a selected rate of increase;

(c) rotating said first file in said root canal to remove pulpal material and to clean and shape said root canal proximal portion, the rotation being continued as the file is axially advanced towards the tooth apex until the file resists further axial advancement;

(d) inserting into said root canal a second file of said set and rotating said second file to remove pulpal material and to clean and shape said root canal in the portion thereof adjacent to said first mentioned proximal portion in step (c) and in the direction towards said tooth apex, the rotation being continued as the file is axially advanced towards the tooth apex until the file resists further axial advancement; and (e) repeating step (d) sequentially using different files selected from said set until said root canal is entirely cleaned and shaped, the cleaning and shaping taking place essentially in the direction from said root canal proximal portion in progressive steps to said tooth apex.

9. A method of cleaning and shaping a root canal according to claim 8 wherein, after the root canal is cleaned and shaped from said proximal portion to said apex portion, the root canal is enlarged in cross-sectional diameters.

10. A method of cleaning and shaping a root canal according to claim 8 wherein said selected rate of taper of said files in said set is greater than 0.02 millimeters per millimeter of axial length.

11. A method of cleaning and shaping a root canal according to claim 8 wherein said tip diameters of said files making up said set increase at a selected arithmetical or geometrical rate.

12. A method of cleaning and shaping a root canal according to claim 8 wherein the steps of rotating said files in said root canal are carried out by sequentially inserting each said file in a power driven hand piece and rotating each said file while said distal end portion is in said root canal.

13. A method of cleaning and shaping a root canal according to claim 8 wherein in the steps of rotating said files in said root canal are carried out manually.

14. A method of cleaning and shaping a root canal in a tooth in preparation for filling the root canal with a filler material, the root canal having a proximal portion adjacent to a tooth pulp chamber and tapering to an apex portion adjacent to the tooth apex, the tooth root canal having a characteristic rate of taper, comprising:

inserting into the root canal a file having spiraled scraping edges formed therein that upon rotation of said file scrapes and planes adjacent root canal walls, the file having a proximal end and a distal end, the file being tapered from adjacent said proximal end to said distal end, the rate of taper being greater than the said characteristic rate of taper of said root canal; and rotating said file and axially advancing said file within said root canal to clean and shape said root canal, the rate of taper of said file relative to said root canal characteristic taper being such that said root canal is shaped by first cleaning and shaping the root canal proximal portion, until advancing said file requires additional axial force.

15. The method of claim 14 wherein said cleaning and shaping is accomplished by a plurality of files having different diameters selected such that said cleaning and shaping progresses from the root canal proximal portion to the root canal apex portion.

16. A method of cleaning and shaping a root canal having a coronal portion and an apex in preparation for filling, comprising:

opening the coronal portion of the canal with a file having a taper and diameter equivalent to a desired finished preparation of the root canal;

advancing one or more files into the root canal, said file having a taper that approximates that of the typical canal and a desired finished apex diameter for the full working length of the canal from the coronal portion to the apex;

advancing one or more files into the root canal, each of said files having a taper that gradually merges the taper selected for the crown opening to the selected apex diameter, from the coronal portion downward to the apex, each said file having a taper greater than that which approximates said canal.

\* \* \* \* \*